US008260559B2

(12) United States Patent
Brussermann et al.

(10) Patent No.: US 8,260,559 B2
(45) Date of Patent: Sep. 4, 2012

(54) SYSTEM AND METHOD FOR MEASUREMENT OF RADIOACTIVITY CONCENTRATION OF A RADIOPHARMACEUTICAL

(75) Inventors: Michael Brussermann, Munster (DE); Guido Schwartenbeck, Munster (DE); Stefan Riese, Munster (DE)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 12/713,954

(22) Filed: Feb. 26, 2010

(65) Prior Publication Data

US 2010/0264326 A1  Oct. 21, 2010

Related U.S. Application Data

(63) Continuation-in-part of application No. 11/862,498, filed on Sep. 27, 2007, now abandoned.

(60) Provisional application No. 60/950,911, filed on Jul. 20, 2007.

(51) Int. Cl.
G01N 15/06 (2006.01)
G01N 33/00 (2006.01)
G01N 33/48 (2006.01)
G01N 31/00 (2006.01)

(52) U.S. Cl. ............... 702/23; 422/68.1; 702/1; 436/43; 436/56; 436/57

(58) Field of Classification Search ................. 422/68.1; 702/1, 23; 436/43, 56, 57
See application file for complete search history.

(56) References Cited

U.S. PATENT DOCUMENTS

| 4,416,865 | A  | * | 11/1983 | Rhodes et al. | 424/1.69 |
|-----------|----|---|---------|---------------|----------|
| 6,447,747 | B1 | * | 9/2002  | Pirotte et al. | 424/1.85 |
| 6,624,415 | B1 | * | 9/2003  | Hattori et al. | 250/336.1 |
| 7,586,102 | B2 | * | 9/2009  | Mourtada et al. | 250/432 PD |
| 2004/0086437 | A1 | * | 5/2004 | Jackson | 422/903 |
| 2005/0232387 | A1 | * | 10/2005 | Padgett et al. | 376/194 |
| 2005/0232861 | A1 | * | 10/2005 | Buchanan et al. | 424/1.11 |
| 2005/0288869 | A1 | * | 12/2005 | Kroll et al. | 702/19 |
| 2011/0178359 | A1 | * | 7/2011 | Hirschman et al. | 600/4 |

* cited by examiner

Primary Examiner — Brian J Sines

(57) ABSTRACT

A system and method for measurement of radioactivity concentration of a radiopharmaceutical are disclosed. The radiopharmaceutical may be a radioactive tracer solution including a tracer solution and a buffer solution. The system may include a vial that receives the tracer solution and the buffer solution; a scale; a radioactivity measuring device; and a controller that determines the radioactive concentration based on a measured radioactivity of the tracer solution and the buffer solution in the vial, and a weight of the tracer solution and the buffer solution in the vial. The method may include the steps of (1) transferring the tracer solution into a vial; (2) measuring a radioactivity of the tracer solution in the vial; (3) determining a weight necessary to achieve a desired radioactivity concentration; and (4) diluting the tracer solution in the vial to the determined weight with a buffer solution.

12 Claims, 2 Drawing Sheets

SYSTEM AND METHOD FOR MEASUREMENT OF RADIOACTIVITY CONCENTRATION OF A RADIOPHARMACEUTICAL

RELATED U.S. APPLICATION DATA

Continuation-in-part of U.S. patent application Ser. No. 11/862,498, filed on Sep. 27, 2007 now abandoned, which was based on and claimed the benefit of U.S. Provisional Patent Appl. No. 60/950,911, filed on Jul. 20, 2007. The disclosure of both applications is incorporated herein by reference.

BACKGROUND OF THE INVENTION

1. Field of the Invention

The present invention generally relates to the measurement of radioactivity, and, more particularly, to a system and method for measurement of radioactivity concentration of a radiopharmaceutical.

2. Description of the Related Art

Medical imaging is used extensively to diagnose and treat patients. A number of modalities are well known, such as Magnetic Resonance Imaging (MRI), Computed Tomography (CT), Positron Emission Tomography (PET), and Single Photon Emission Computed Tomography (SPECT). These modalities provide complementary diagnostic information. For example, PET and SPECT scans illustrate functional aspects of the organ or region being examined and allow metabolic measurements, but delineate the body structure relatively poorly. On the other hand, CT and MRI images provide excellent structural information about the body, but provide little functional information.

PET and SPECT are classified as "nuclear medicine" because they measure an emission of a radioactive tracer that has been injected into a patient. After the radioactive tracer, or radiopharmaceutical, is injected, it is absorbed by the blood or a particular organ of interest. The patient is then moved into the PET or SPECT detector that measures the emission of the radiopharmaceutical and creates an image from the characteristics of the detected emission.

A significant step in conducting a PET or SPECT scan is the step of acquiring the radioactive tracer. Examples of radiopharmaceuticals include FDG (2-[$^{18}$F]-fluoro-2-deoxyglucose), other $^{18}$F based fluorinated tracers, $^{13}$N ammonia, $^{11}$C based tracers, $^{15}$O gas, and $^{15}$O water, and others.

The half lives of these radiopharmaceuticals range from two minutes to two hours. Thus, the injection into the patient and the imaging must take place within a very short time period after production of the radiopharmaceutical. Because of this, it is important for the technician operating the medical imaging device to know the radioactive concentration, as well as the time and date that the radioactive concentration was measured. This may be determined by measuring the total radioactivity of a tracer in an ionization chamber, and taking an aliquot in a syringe to measure the activity concentration. Either the aliquot is put into an ionization chamber or the change of radioactivity of the bulk solution is determined. With the known volume of the aliquot and the measured radioactivity, radioactivity concentration can then be determined.

SUMMARY OF THE INVENTION

A system and method for measurement of radioactivity concentration of a radiopharmaceutical are disclosed. According to one embodiment, the radiopharmaceutical may be radioactive tracer solution including a tracer solution and a buffer solution. The system includes a vial that receives the tracer solution and the buffer solution; a scale; a radioactivity measuring device; and a controller that determines the radioactive concentration based on a measured radioactivity of the tracer solution and the buffer solution in the vial, and a weight of the tracer solution and the buffer solution in the vial.

In one embodiment, the tracer solution may comprise 2-[18F]-fluoro-2-deoxyglucose. The buffer solution may be a sodium chloride solution. The tracer solution may be provided to the vial by tubing.

The system may further comprise a gas source in communication with the vial and the buffer solution. The system may also comprise a fill line in communication with the vial. The system may also comprise a plurality of valves that direct the flow of at least a gas and a liquid. The system may also comprise a plurality of filters for filtering at least one of a gas and a liquid.

The method for measurement of radioactivity concentration of a radiopharmaceutical may include the steps of (1) transferring the tracer solution into a vial; (2) measuring a radioactivity of the tracer solution in the vial; (3) determining a weight necessary to achieve a desired radioactivity concentration; and (4) diluting the tracer solution in the vial to the determined weight with a buffer solution.

The method may also include the steps of determining an initial weight for the vial, and determining a radiation base noise level.

The method may also include the step of mixing the tracer solution and the buffer solution.

The step of transferring a tracer solution into a vial may include opening a valve between a source of the tracer solution and the vial, and filtering the tracer solution.

The step of diluting the tracer solution in the vial to the determined weight with a buffer solution may include pressurizing a container containing the buffer solution with a gas from a gas source, opening a valve between the container containing the buffer solution and the vial, and transferring the buffer solution to the vial.

The step of mixing the tracer solution and the buffer solution may include opening a valve between a gas source and the vial, filtering the gas from the gas source, and bubbling the gas through the tracer solution and buffer solution.

It is a technical advantage of the present invention that a system and method of measuring radioactivity concentration of a radiopharmaceutical are disclosed. It is another technical advantage of the present invention that the tubing that communicates the different parts of the system may be replaceable. It is another technical advantage of the present invention that the system and method minimize human interaction.

BRIEF DESCRIPTION OF THE DRAWINGS

For a more complete understanding of the present invention, the objects and advantages thereof, reference is now made to the following descriptions taken in connection with the accompanying drawings in which.

DETAILED DESCRIPTION OF PREFERRED EMBODIMENTS

Figure 1:
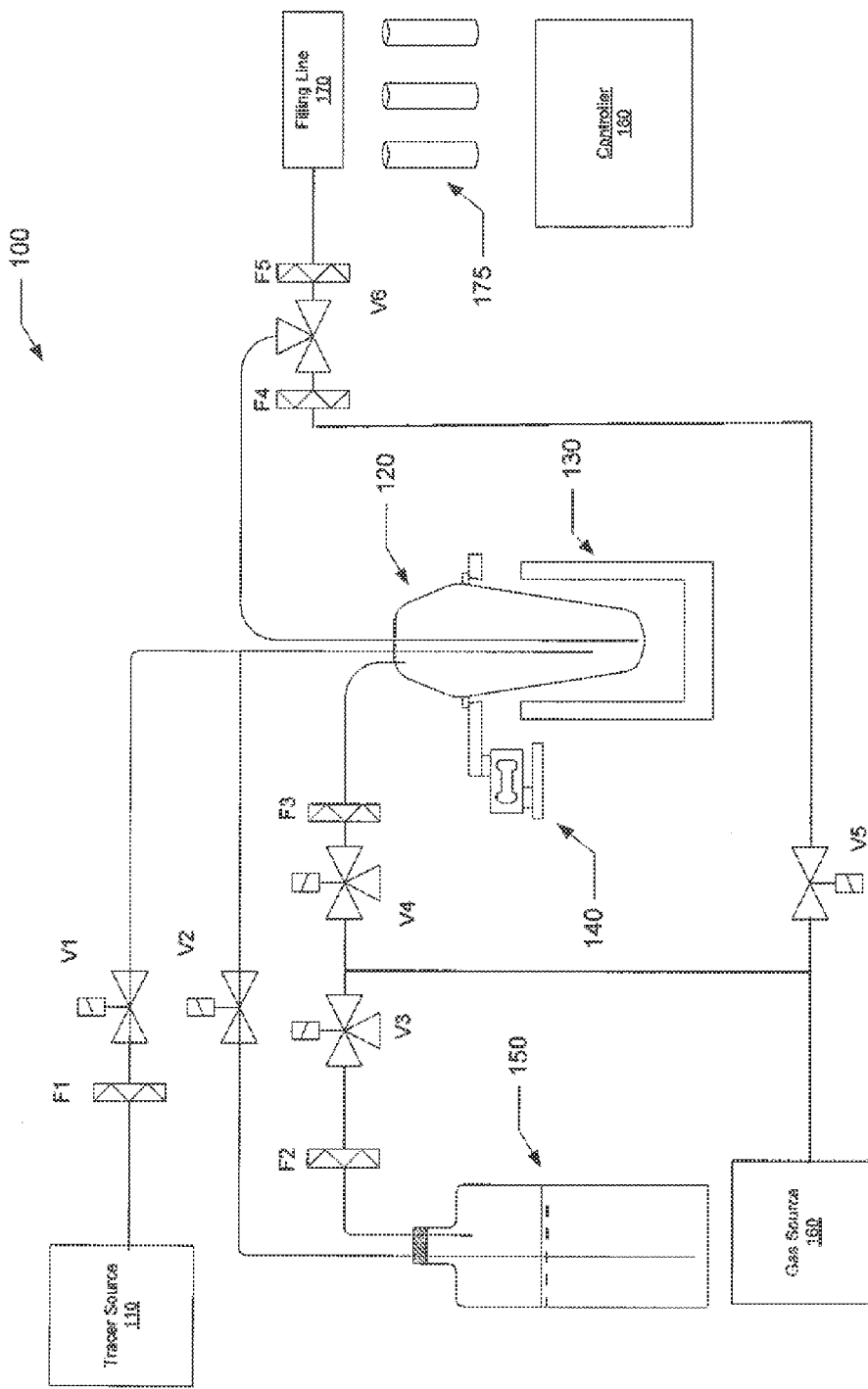
FIG. 1 is a block diagram of a system for measurement of a radioactivity concentration of a radiopharmaceutical according to one embodiment of the present invention.
Figure 2:
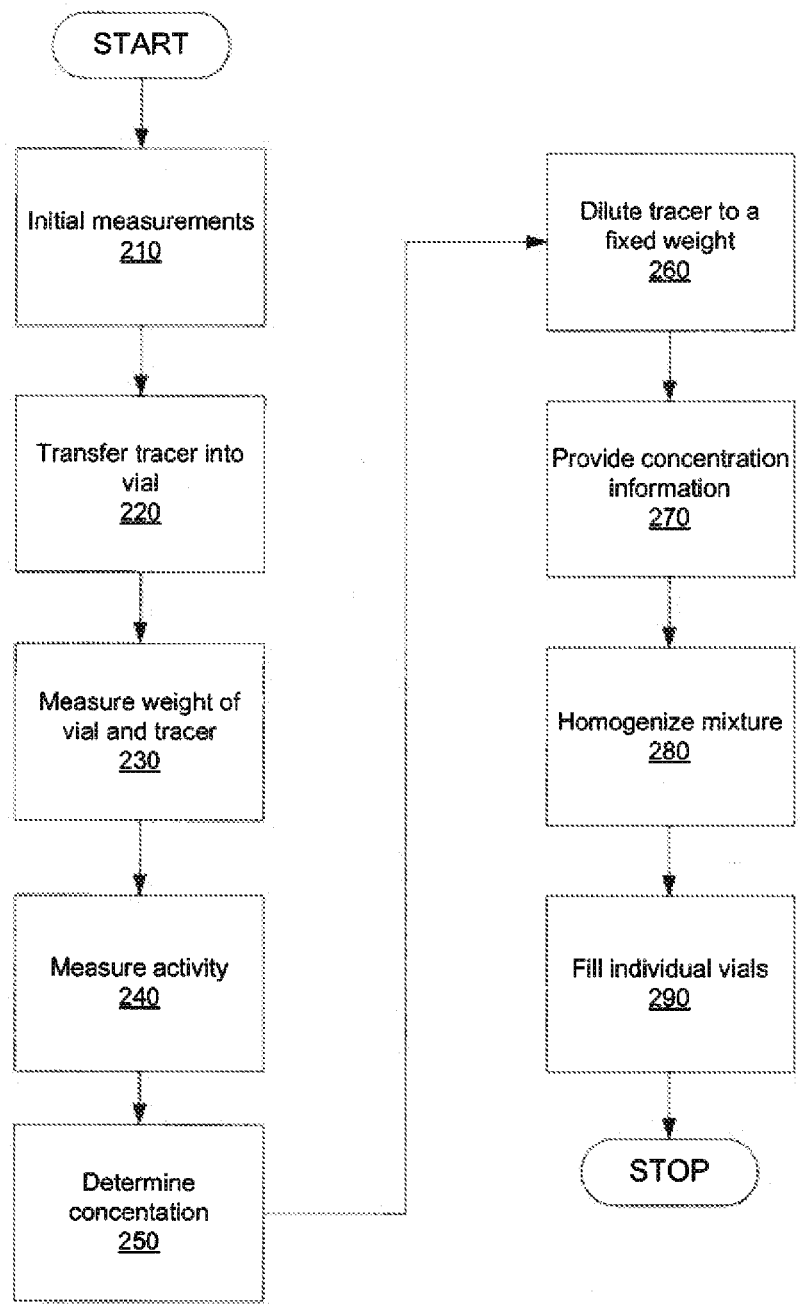
FIG. 2 is a flowchart depicting a method for measurement of a radioactivity concentration of a radiopharmaceutical according to one embodiment of the present invention.

Preferred embodiments and their advantages may be understood by referring to FIGS. 1-2, wherein like reference numerals refer to like elements.

Disclosed herein is a novel system and method for making this determination quickly and with no, or minimal, human interaction.

The present invention may be implemented in a transportable manufacturing facility for radioactive materials. An example of such is described in U.S. Patent Publ. No. 2004/0086437, the disclosure of which is incorporated by reference in its entirety. In one embodiment, such a transportable manufacturing facility includes a building structure which encloses working space of the manufacturing facility. This building structure is designed to house a cyclotron and to be transportable by truck, rail or other mode of transportation to a destination site. The manufacturing facility is substantially equipped during transport to produce and package a radiopharmaceutical, except for lacking a cyclotron during transport. This production of the radiopharmaceutical includes a method for measurement of a radioactivity concentration of a radiopharmaceutical as described by the present application.

Referring to FIG. 1, a system for the measurement of radioactivity concentration and total radioactivity of a radiopharmaceutical is disclosed. The radiopharmaceutical may be a radioactive tracer solution including a tracer solution 110 and a buffer solution 150. According to one embodiment, system 100 includes bulk vial 120, ionization chamber 130, scale 140, gas source 160, and filling line 170. Filters F1, F2, F3, F4, and F5 may be provided to system 100. In addition, valves V1, V2, V3, V4, V5, and V6 direct the flow of gasses and/or fluids within system 100. Controller 180 controls the operation of valves V1, V2, V3, V4, V5, and V6, ionization chamber 130, and scale 140. For simplicity, the electrical connections between controller 180, valves V1, V2, V3, V4, V5, and V6, ionization chamber 130, and scale 140 are not shown.

As shown in FIG. 1, system 100 includes tubing between tracer source 110, vial 120, buffer solution 150, gas source 160, and filling line 170. In one embodiment, the tubing may be surgical tubing, including silicon tubing as specified by USP class VI or Pharm. Eur. III. In another embodiment, the tubing may be any smooth tubing. In one embodiment, the surgical tubing may be removeable and replaced as necessary and desired, such as for each new batch of tracer.

Tracer source 110 may be a source of any radioactive tracer. For example, tracer source 110 may be a source of FDG (2-[$^{18}$F]-fluoro-2-deoxyglucose), any other 18F-based fluorinated tracer, $^{13}$N ammonia, $^{11}$C carbon-based tracers, $^{15}$O water, etc. In one embodiment, tracer source 110 may be the output of a synthesizer.

In one embodiment, bulk vial 120 may be a bespoke container made from polycarbonate (Makrolon Rx1805).

Although system 100 is described as including bulk vial 120, which may then be used to fill smaller vials, it should be recognized that smaller vials (not shown) may be used in place of bulk vial 120. In one embodiment, these smaller vials may be sized for individual dosages.

Ionization chamber 130 is used to measure the radioactivity of the material in bulk vial 120. In one embodiment, ionization chamber may be QQQ-624, manufactured by Veenstra Instruments, The Netherlands.

In one embodiment, ionization chamber 130 may also measure background radiation before bulk vial 120 is filled with the tracer in order to determine a baseline radioactivity.

Scale 140 measures the weight of bulk vial 120 and/or the contents of bulk vial 120. In one embodiment, scale 140 may have a maximum load of 1500 g, and manufactured by Tedea-Huntleigh.

Buffer solution 150 may include any isotonic solution, i.e., a solution that has an equal amount of dissolved solute in it compared to the human blood. In one embodiment, a sodium chloride solution, may be used. In another embodiment, buffer solution 150 may be a phosphoric buffer solution. However, any injectable solution may be used to dilute the tracer.

Gas source 160 may be a source for any inert gas. In one embodiment, gas source 160 may be a source of $N_2$.

Filling line 170 is used to fill individual vials 175 for transport of the solution to the patient.

Filters F1, F2, F3, F4, and F5 are provided in order to filter gas and liquid as they travel through system 100. In one embodiment, polytetrafluoroethylene (PTFE) filters may be used to filter gasses. For example, filters F2, F3 and F4 may be PTFE filters. Other filters for filtering gasses may be used as necessary and desired.

In one embodiment, polyethersulfone filters may be used to filter liquids. For example, filter F1 may be filter type 65770, manufactured by Filtertek, and F5 may be filter type SLGP 033RB manufactured by Milipore. Other filters for filtering liquids may be used as necessary and desired.

As noted above, valves V1, V2, V3, V4, V5, and V6 direct the flow of gasses and fluids within system 100. In one embodiment, V1, V2, V3, V4 and V5 are pinch valves that pinch tubing in order to disrupt fluid or gas flow. An example of a suitable pinch valve is model S104 08 Z030A 24VDC, manufactured by Sirai.

In one embodiment, V6 may be a medical valve. An example of a suitable medical valve is Type 562416 manufactured by Elcam. Valve V6 may be a three position valve, providing two directions of flow and an "off" position.

Other valves may be used as necessary and/or desired.

As noted above, controller 180 controls the operation of valves V1, V2, V3, V4, V5, and V6, ionization chamber 130, and scale 140. In one embodiment, controller 180 may be a microprocessor-driven controller. For example, a PLC, such as B&R series 2003, manufactured by B&R Industrieelektronik, Austria, may be used.

In another embodiment, at least some of valves V1, V2, V3, V4, V5, and V6 may be manually controlled.

Referring to FIG. 2, a method for measurement of radioactivity concentration and total radioactivity of a radiopharmaceutical is disclosed. Although the method depicted in FIG. 2 will be described in the context of the system of FIG. 1, it should be recognized that the method is not limited to use with such a system.

In step 210, initial measurements are made. In one embodiment, the weight of bulk vial 120 without the tracer solutions is determined. The background radiation level may also be measured in order to determine a radiation base noise level.

In step 220, the tracer is transferred from tracer source 110 into bulk vial 120. In one embodiment, this may be achieved by opening valve V1 and allowing gas pressure to force the tracer through filter F1 into bulk vial 120.

In step 230, the weight of bulk vial 120 may be monitored as the transfer proceeds. Once a desired weight is achieved and/or time has passed, valve V1 is closed.

In step 240, radioactivity is measured. In one embodiment, this may be accomplished by using, for example, ionization chamber 130. The radiation base noise level measured in step 210 may be subtracted from the measured radiation level to determine the radioactivity of the tracer solution.

In step 250, the weight necessary to achieve the desired radioactive concentration is determined. This weight may be determined by multiplying the desired activity concentration by the measured activity, and then subtracting from the result the weight of the tracer.

In step 260, the tracer is diluted to the desired radioactive concentration. In one embodiment, this may be achieved by pressurizing the bottle containing buffer solution 150 with a gas from gas source 160 by opening valve V3. Valve V2 is then opened, and buffer solution is forced into bulk vial 120 through Filter F2. Once the predetermined weight is reached, V2 and V3 are closed.

In step 270, the diluted tracer solution may be mixed to achieve a homogenous concentration. In one embodiment, the mixing is achieved with gas bubbles. For example, valve V5 may be opened, and valve V6 may be biased to allow gas from gas source 160 to be transferred to bulk vial 120. The resulting gas bubbles create a homogenous solution.

Valve V5 may be shut after the passage of a predetermined amount of time, or after a predetermined volume of gas has passed.

In step 280, an indication of the radioactivity, volume and radioactivity concentration may be provided. This may be provided visually via a display, or it may be provided on a label. Other information, including tracer identification, time and date of measurement, etc. may be provided.

In step 290, individual vials may be filled with an amount of radioactive tracer. In one embodiment, this may be achieved by opening valve V4, and biasing valve V6 to allow the passage of fluid from bulk vial 120 to filling line 170. Gas from gas source 160 forces the radioactive tracer to exit filling line 170 into individual vials 175.

After filling, the remaining radioactivity may be flushed with buffer solution with gas pressure, by opening valve V3, V2 and V6 and positioning the outlet of filter F5, or filing line 170, over, for example, a sink.

Other embodiments, uses, and advantages of the present invention will be apparent to those skilled in the art from consideration of the specification and practice of the invention disclosed herein. The specification and examples should be considered exemplary only.

What is claimed is:

1. A method for achieving a radioactivity concentration of a radiopharmaceutical comprising a tracer solution and a buffer solution, the method comprising:
    transferring the tracer solution into a vial;
    measuring a radioactivity of the tracer solution in the vial;
    determining a weight of tracer solution and buffer solution necessary to achieve a desired radioactivity concentration; and
    diluting the tracer solution in the vial to the determined weight with a buffer solution.

2. The method of claim 1, further comprising:
    determining a radiation base noise level.

3. The method of claim 2, wherein the step of measuring a radioactivity of the tracer solution in the vial comprises:
    determining the radioactivity of the tracer solution in the vial; and
    subtracting the radiation base noise level from the radioactivity of the tracer solution in the vial.

4. The method of claim 1, further comprising:
    determining the weight of the tracer solution.

5. The method of claim 4, wherein the step of determining the weight of the tracer solution comprises:
    measuring an initial weight for the vial;
    measuring a weight of the tracer solution and the vial; and
    subtracting the initial weight of the vial from the combined weight of the tracer solution and the vial.

6. The method of claim 4, wherein the step of determining a weight necessary to achieve a desired radioactivity concentration comprises:
    multiplying a desired activity concentration by the measured radioactivity, and subtracting the weight of the tracer solution.

7. The method of claim 1, further comprising:
    mixing the tracer solution and buffer solution in the vial.

8. The method of claim 1, wherein the step of transferring the tracer solution into a vial comprises:
    opening a valve between a source of the tracer solution and the vial; and
    filtering the tracer solution.

9. The method of claim 1, wherein the step of diluting the tracer solution in the vial to the determined weight with a buffer solution comprises:
    pressurizing a container containing the buffer solution with a gas from a gas source;
    opening a valve between the container containing the buffer solution and the vial; and
    transferring the buffer solution to the vial.

10. The method of claim 7, wherein the step of mixing the tracer and buffer solution comprises:
    opening a valve between a gas source and the vial;
    filtering the gas from the gas source; and
    bubbling the gas through the tracer solution and buffer solution in the vial.

11. A method for of achieving a radioactivity concentration of a radiopharmaceutical comprising a tracer solution and a buffer solution, the method comprising:
    transferring the tracer solution into a vial;
    measuring a radioactivity of the tracer solution in the vial comprising determining a radiation base noise level, determining the radioactivity of the tracer solution in the vial, and subtracting the radiation base noise level from the radioactivity of the tracer solution in the vial;
    determining a weight necessary to achieve a desired radioactivity concentration comprising determining the weight of the tracer solution, multiplying a desired activity concentration by the measured radioactivity, and subtracting the weight of the tracer solution; and
    diluting the tracer solution in the vial to the determined weight with a buffer solution.

12. The method of claim 11, wherein the step of determining the weight of the tracer solution comprises measuring an initial weight for the vial, measuring a weight of the tracer solution and the vial, and subtracting the initial weight of the vial from the combined weight of the tracer solution and the vial.

* * * * *